United States Patent [19]

D'Silva

[11] 4,234,580
[45] Nov. 18, 1980

[54] CARBAMATE THIOSULFENYLCARBAMOYL FLUORIDE COMPOUNDS

[75] Inventor: Themistocles D. J. D'Silva, South Charleston, W. Va.

[73] Assignee: Union Carbide Corporation, New York, N.Y.

[21] Appl. No.: 781,996

[22] Filed: Mar. 28, 1977

[51] Int. Cl.$^3$ ............... C07C 124/04; C07C 125/06; A01N 9/12; C07C 125/04
[52] U.S. Cl. .................. 424/246; 560/148; 560/132; 260/544 C; 560/133; 560/134; 260/326.2; 560/135; 560/136; 260/340.3; 564/265; 260/340.5 R; 260/340.6; 260/340.9 R; 260/346.73; 260/347.2; 260/465 D; 424/277; 424/248.5; 424/248.51; 424/248.52; 424/270; 424/276; 424/278; 424/282; 424/283; 424/285; 424/327; 424/300; 548/184; 544/58.2; 544/164; 549/21; 549/38; 549/51; 549/60; 549/39; 549/22; 549/68; 560/137
[58] Field of Search ............... 560/137, 148, 132, 133, 560/134, 135, 136; 424/300, 277, 246, 248.5, 248.51, 248.52, 270, 276, 278, 282, 283, 285, 327; 260/551 S, 544 C, 326.2, 340.3, 340.5 R, 340.6, 340.9 R, 346.73, 347.2, 465 D, 465.42, 566 AC; 548/184; 544/58.2, 164; 549/21, 38, 14, 30, 51, 60, 39, 22, 68

[56] References Cited

U.S. PATENT DOCUMENTS

| | | | |
|---|---|---|---|
| 3,326,967 | 6/1967 | Rätz et al. | 560/137 |
| 3,794,733 | 2/1974 | Brown | 424/300 |
| 3,812,174 | 5/1974 | Brown et al. | 424/300 X |
| 3,856,786 | 12/1974 | Huber | 560/148 X |
| 3,968,232 | 7/1976 | Siegle et al. | 424/300 X |
| 3,974,591 | 3/1976 | Rizzo et al. | 260/551 SX |
| 3,998,963 | 12/1976 | Durden et al. | 424/298 |
| 4,004,031 | 1/1977 | Drabek | 260/551 S X |
| 4,058,549 | 11/1977 | D'Silva | 260/544 C |
| 4,072,751 | 2/1978 | D'Silva | 260/561 S |

FOREIGN PATENT DOCUMENTS

2045440  3/1972  Fed. Rep. of Germany ........... 560/137

OTHER PUBLICATIONS

Fahmy et al. J. Agr. Food Chem. 22 (1974) p. 59.
Wagner et al. Synthetic Organic Chem. John Wiley & Sons N.Y. N.Y.; 1955, pp. 481–482.

*Primary Examiner*—Arthur P. Demers
*Attorney, Agent, or Firm*—Dale L. Carlson

[57] ABSTRACT

Carbamate thiosulfenylcarbamoyl fluoride compounds are insecticidal and miticidal compounds and are also useful intermediates in the preparation of pesticidally active bis-carbamate disulfide compounds.

32 Claims, No Drawings

CARBAMATE THIOSULFENYLCARBAMOYL FLUORIDE COMPOUNDS

This invention relates to carbamate thiosulfenylcarbamoyl fluoride compounds and the methods of preparing them. This invention is also directed to insecticidal and miticidal compositions comprising an acceptable carrier and an insecticidally or miticidally effective amount of a compound of this invention as well as to a method of controlling insects and mites which comprises subjecting them to an insecticidally and miticidally effective amount of a compound of this invention.

More particularly, this invention relates to compounds of the formula:

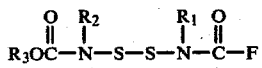

wherein:
$R_1$ and $R_2$ are the same or different and are alkyl groups having from one to four carbon atoms;
$R_3$ is:
(A) alkyl, cycloalkyl, alkenyl or alkyenyl; or
(B) dihydrobenzofuranyl, naphthyl, tetrahydronaphthyl, benzothienyl, indanyl, benzodioxalanyl, benzofuranyl, benzodioxanyl or methylenedioxyphenyl all of which may be either unsubstituted or substituted with one or more alkyl groups; or
(C) phenyl, either unsubstituted or substituted with one or more halo, cyano, nitro, cycloalkyl, alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino, alkoxy; or
(D)

or $A\overset{\frown}{C}=N$, wherein:
$R_4$ is hydrogen, alkyl, alkylthio, alkylsulfinyl, alkylsulfonyl or cyano;
$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl or dialkyloaminocarbonyl all of which may be unsubstituted or, except aminocarbonyl, substituted with one or more cyano, nitro, alkylthio, alkylsulfonyl, alkoxy, aminocarbonyl alkylaminocarbonyl, dialkylaminocarbonyl or $R_5$ is a

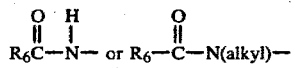

group where $R_6$ is hydrogen, alkyl or alkoxy;
A is a divalent alkylene chain having from 2 to 24 aliphatic carbon atoms completing a five or six membered ring structure which includes one, two or three groups selected from the group consisting of divalent oxygen, sulfur, sulfinyl, sulfonyl, amino, alkylamino, alkylimino or carbonyl groups;
with the proviso that $R_3$, $R_4$, $R_5$ and $R_6$ substituents individually may not include more than eight aliphatic carbon atoms.

The following miticidally and insecticidally active compounds are illustrative of the compounds of this invention all of which can be conveniently prepared by the process of this invention simply by selecting appropriate starting materials for use in the procedures described below:

2,3-Dihydro-2-methyl-7-[N-methyl-N-(N'-methyl-N'-fluoroformylaminothiosulfenyl)carbamoyloxy]benzofuran.

1-[N-Methyl-N-(N'-methyl-N'-fluoroformylaminothiosulfenyl)carbamoyloxy]5,6,7,8-tetrahydronaphthalene.

2-Methyl-2-methylsulfonylpropionaldehyde O-[N-methyl-N-(N'-fluoroformylaminothiosulfenyl)carbamoyl]oxime.

1-Isopropylthioacetaldehyde O-[N-methyl-N-(N'-methyl-N'-fluoroformylaminothiosulfenyl)carbamoyl]oxime.

2-Methyl-2-methoxypropionaldehyde O-[N-methyl-N-(N'-methyl-N'-fluoroformylaminothiosulfenyl)carbamoyl]oxime.

1-(2-Cyanoethylthio)acetaldehyde O-[N-methyl-N-(N'-methyl-N'-fluoroformylaminothiosulfenyl)carbamoyl]oxime.

2-Methyl-2-cyanopropionaldehyde O-[N-methyl-N-(N'-methyl-N'-fluoroformylaminothiosulfenyl)carbamoyl]oxime.

1-Methylthio-1-dimethylcarbamoylformaldehyde O-[N-methyl-N-(N'-methyl-N'-fluoroformylaminothiosulfenyl)carbamoyl)]oxime.

2-[[O-[N-methyl-N-(N'-methyl-N'-fluoroformylaminothiosulfenyl)carbamoyl]oximino]]-4-methyl-tetrahydro-1,4-thiazin-3-one.

1-Methylthio-3,3-dimethylbutanone-2 O-[N-methyl-N-(N'-methyl-N'-fluoroformylaminothiosulfenyl)carbamoyl]oxime.

2-[[O-[N-methyl-N-(N'-methyl-N'-fluoroformylaminothiosulfenyl)carbamoyl]oximino]]-1,3-dithiolane.

4-[[O-[N-methyl-N-(N'-methyl-N'-fluoroformylaminothiosulfenyl)carbamoyl]oximino]]-5,5-dimethyl-1,3-dithiolane.

4-[[0-[N-methyl-N-(N'-methyl-N'-fluoroformylaminothiosulfenyl)carbamoyl]oximino]]-5-methyl-1,3-oxathiolane.

2-[[O-[N-methyl-N-(N'-methyl-N'-fluoroformylaminothiosulfenyl)carbamoyl]oximino]]-3,3-dimethyl-1,4-dithiane.

2-[[O-[N-methyl-N-(N'-methyl-N'-fluoroformylaminothiosulfenyl)carbamoyl]oximino]]-3-isopropylthiazolidin-4-one.

2-[[O-[N-methyl-N-(N'-methyl-N'-fluoroformylaminothiosulfenyl)carbamoyl]oximino]]-4,5,5-trimethylthiazolidin-3-one.

4-Dimethylamino-3,5-xylyl-N-methyl-N-(N'-methyl-N'-fluoroformylaminothiosulfenyl)carbamate.

4-Methoxycarbonylamino-3,5-xylyl-N-methyl-N-(N'-methyl-N'-fluoroformylaminothiosulfenyl)carbamate.

2-Isopropoxyphenyl-N-methyl-N-(N'-methyl-N'-fluoroformylaminothiosulfenyl)carbamate.

3-sec-Butylphenyl-N-methyl-N-(N'-methyl-N'-fluoroformylaminothiosulfenyl)carbamate.

3,4-Xylyl-N-methyl-N-(N'-methyl-N'-fluoroformylaminothiosulfenyl)carbamate.

3,4-Methylenedioxyphenyl-N-methyl-N-(N'-methyl-N'-fluoroformylaminothiosulfenyl)carbamate.

4-Methylthio-3,5-xylyl-N-methyl-N-(N'-methyl-N'-fluoroformylaminothiosulfenyl)carbamate.

2-Dioxalanylphenyl-N-methyl-N-(N'-methyl-N'-fluoroformylaminothiosulfenyl)carbamate.

1-Methylthioacetaldehyde O-[N-butyl-N-(N'-methyl-N'-fluoroformylaminothiosulfenyl)carbamoyl]oxime.

2-Methyl-2-methylthiopropionaldehyde O-[N-methyl-N-(N'-isopropyl-N'-fluoroformylaminothiosulfenyl)carbamoyl]oxime.

2-Methyl-2-methoxypropionaldehyde O-[N-methyl-N-(N'-butyl-N'-fluoroformylaminothiosulfenyl)carbamoyl]oxime.

2,4-Dinitro-6-sec-butylphenyl-N-methyl-N-(N'-methyl-N'-fluoroformylaminothiosulfenyl)carbamate.

3-Isopropylphenyl-N-methyl-N-(N'-methyl-N'-fluoroformylaminothiosulfenyl)carbamate.

4-Isopropylphenyl-N-methyl-N-(N'-methyl-N'-fluoroformylaminothiosulfenyl)carbamate.

1-Cyano-2,2-dimethylpropionaldehyde O-[N-methyl-N-(N'-methyl-N'-fluoroformylaminothiosulfenyl)carbamoyl]oxime.

1-Methylsulfonyl-3,3-dimethylbutanone-2 O-[N-methyl-N-(N'-methyl-N'-fluoroformylaminothiosulfenyl)carbamoyl]oxime.

3-Methylsulfonylbutanone-2 O-[N-methyl-N-(N'-methyl-N'-fluoroformylaminothiosulfenyl)carbamoyl]oxime.

N-Methyl-N-(N'-methyl-N'-dodecanoylaminothiosulfenyl)carbamoyl fluoride.

Many of the compounds of this invention exhibit insecticidal and miticidal activity to a lesser or greater extent. Accordingly, these compounds are useful for the control of insect and mite pests. Some of these compounds exhibit very high levels of miticidal and insecticidal activity in extremely small dosages while others require larger dosages to be effective.

In general, the compounds of this invention are either totally lacking in phytotoxicity or exhibited only minimal phytotoxicity with respect to economically important crop species tested. These compounds also exhibit substantially reduced levels of mammalian toxicity as compared to known pesticidal compounds having a comparable spectrum of activity against insect and mite pests.

All the compounds within the purview of the generic formula set forth above are useful as intermediates in the preparation of insecticidal, miticidal and nematocidal compounds having a broad spectrum of pesticidal activity, improved mammalian and plant safety and improved residual properties. For example 1-methylthio acetaldehyde O-[N-methyl-N-(N'-methyl-N'-fluoroformylaminothiosulfenyl)carbamoyl]oxime may be reacted with 2-oximino-1,4-dithiane in the presence of triethylamine as the acceptor to yield N-[1-methylthioacetaldehyde O-(N-methylcarbamoyl)oxime] N-[2-O-(N-methylcarbamoyl)oximino-1,4-dithiane]disulfide, which exhibits outstanding insecticidal and miticidal properties. The compounds of this invention may also be reacted with alcohols and hydroxylated aryl compounds to form the corresponding insecticidally and miticidally active bis-carbamate compound. These reactions as well as the utility of the pesticidally active biscarbamate compounds prepared thereby are described in more detail in United States Patent Application Ser. No. 781,986, Docket Number 11332, entitled "UNSYMMETRICAL BIS-CARBAMATE DISULFIDE COMPOUNDS" now U.S. Pat. No. 4,166,864, and United States Patent Application Ser. No. 781,987, Docket Number 11333, entitled UNSYMMETRICAL BIS-CARBAMATE DISULFIDE COMPOUNDS now U.S. Pat. No. 4169894, both filed concurrently herewith.

Preferred because of their higher levels of insecticidal and miticidal activity and because of their utility as intermediates in the preparation of other pesticidally active compounds are the compounds of this invention in which $R_1$ and $R_2$ are methyl;

$R_3$ is:

(a) alkyl, naphthyl, dihydrobenzofuranyl dihydrobenzofuranyl substituted with one or more alkyl, 5, 6, 7, 8-tetrahydronaphthyl, phenyl or phenyl substituted with one or more alkyl, alkynyloxy alkoxy or alkylthio;

(b)

or $A\overset{\frown}{C}=N-$, wherein:

$R_4$ is hydrogen, alkyl, alkylthio or cyano, $R_5$ is alkyl, alkylthio, alkylsulfinyl, alkylsulfonyl, alkylthioalkyl, alkylsulfinylalkyl, alkylsulfonylalkyl or cyanoalkylthio;

A is a divalent alkylene claim having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxazin-3-one, 2-oximino-1,3,5-trithiane, 4-oximino-1,3,5-oxathiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazine-5-one ring structure, wherein sulfur may be in any of its oxidation states.

The carbamate thiosulfenylcarbamoyl fluoride compounds of this invention can be prepared by a variety of methods. One preferred method is illustrated by the reaction scheme set forth below in which $R_1$, $R_2$ and $R_3$ are as described above:

METHOD I

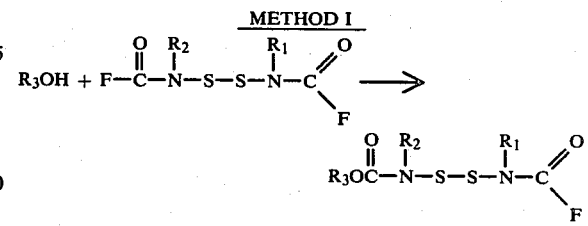

In the procedure illustrated in METHOD I, one equivalent of the hydroxylated reactant is reacted with an equivalent of the bis-(N-alkyl-N-fluorocarbonylamino)disulfide reactant in an appropriate solvent in the presence of at least one equivalent of an acid acceptor. Normally an aprotic organic solvent is employed as the reaction solvent. Illustrative of aprotic organic solvents which are suitable or reaction solvents in the practice of the preferred embodiments of this reaction are saturated and unsaturated aliphatic and aromatic hydrocarbons, e.g. hexane, cyclohexane, octane, dodecane, naphtha, decalin, kerosene, tetrahydronapthalene, cycloheptane, alkylcycloalkane, benzene, toluene, xylene, naphthalene, alkylnapthalene, or the like; ethers such as tetrahydrofuran, tetrahydropyran, diethyl ether, dioxane, 1,2-dimethoxybenzene, 1,2-ethoxybenzene, the mono and dialkyl ethers of ethylene glycol, of dipropylene glycol, of butylene glycol, of diethylene glycol, of dipropylene glycol, or chlorinated aliphatic hydrocarbons as for example, chloroform, dichloromethane, methylene dichloride, 1,1-dichloroethane, carbon tetrachloride or the like.

The acid acceptor utilized in the conduct of the reaction of METHOD I may be either an organic or inorganic base. Illustrate of organic bases that are useful as acid acceptors are tertiary amines, alkali metal alkoxides or the like. Bases such as sodium hydroxide, potassium hydroxide or the like are illustrative of inorganic bases which are useful in the conduct of this reaction. Preferred acid acceptors are aromatic and aliphatic tertiary amines, such as triethylamine, pyridine, trimethylamine, 1,4-diazobicyclo[2.2.2]octane and the like.

When an inorganic base is used as the acid acceptor, phase transfer agents may be used to facilitate the transfer of the acid acceptor and the reactants across the organic/inorganic phase interface. Illustrative of useful phase transfer agents are crown ether compounds, quaternary ammonium halide compounds or the like.

The reaction temperature is not critical and can be varied over a wide range. The reaction is preferably conducted at a temperature of from about −30° C. and upwards to approximately 120° C. Particularly preferred reaction temperatures are from about 0° C. to about 75° C.

Reaction pressures are not critical. The process can be conducted at either subatmospheric, atmospheric or superatmospheric pressure. For convenience the reaction is usually conducted at atmospheric or autogeneous pressure.

Compounds of this invention in which $R_2$, $R_3$ or A includes a sulfinyl or sulfonyl moiety can be conveniently prepared by the selective oxidation of the sulfide linkage of the corresponding thio compound at an appropriate point in the synthetic procedure. For example 1-methylsulfonylacetaldehyde O-[N-methyl(N′-methyl-N′-fluoroformylaminothiosulfenyl)carbamoyl]oxime can be conveniently prepared either by selectively oxidising 1-methylthioacetaldoxime with peracetic acid prior to carbamoylation or by selectively oxidising 1-methylthioacetaldehyde O-[N-methyl-N-(N′-methyl-N′-fluoroformylaminothiosulfenyl)carbamoyl]oxime subsequent to carbamoylation.

Oxime precursors of the formula:

in which $R_2$ and $R_3$ are described above, can be conveniently prepared according to a variety of methods. For example, 2-methylthio-2-methylpropionaldoxime can be prepared by chlorinating 2-methylpropanol to form 2-chloro-2-methylpropanal which is then treated with sodium methylmerceptide to form 2-methylthio-2-methyl-propanol. 2-Methylthio-2-methyl-propanol is then treated with hydroxylamine hydrochloride to form the desired oxime precursor. The above disclosed method together with other methods useful for preparing oxime precursors are described in more detail in the U.S. Pat. Nos. 3,843,669; 3,217,036; 3,217,037; 3,400,153; 3,536,760; 3,576,843 and 3,790,560 and Belgium Pat. No. 813,206.

Alicyclic oxime precursors of the formula:

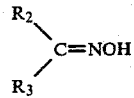

used in the preparation of the disulfide compounds of this invention can be prepared by a variety of methods, the choice of method being influenced to a large extent by the types and number of hetero groups included within the alicyclic ring. For example:

A. 2-oximino-1,3,5-trithiane, 4-oximino-1,3-oxazolidin-4-one, 4-oximino-1,3,5-oxadithiane and 2-oximino-1,4-oxazine-3-one compounds can be conveniently prepared by sequentially treating the corresponding 1,3,5-trithiane, 1,3-oxazolidin-4-one, 1,3,5-oxadithiane or 1,4-oxazin-3-one compound with a base and an alkyl nitrite ester followed by neutralization with a suitable organic or inorganic acid. For example, 2-oximino-4-methyltetrahydro-1,4-oxazin-3-one can be prepared by treating 4-methyltetrahydro-1,4-oxazin-3-one with potassium t-butoxide followed by the addition of isobutyl nitrite. The reaction is conducted in anhydrous tetrahydrofuran. After the reaction has gone to completion in about 3 hours the resulting oxime salt is neutralized with hydrochloric acid.

B. 2-oximino-tetrahydro-1,4-thiazine-3-one compounds can be prepared by reacting ethoxycarbonylformhydroxamoyl chloride with the sodium salt of an appropriately substituted alkylaminoalkane mercaptan in an aprotic solvent, such as benzene, chloroform and the like. This reaction is described in more detail in U.S. Pat. No. 3,790,560.

C. 3-Oximino-1,4-oxathiane and 4-oximino-1,3-oxathiolane compounds can be prepared by sequentially treating bis-(2-bromoalkyl)ether with sodium nitrite and sodium thioacetate to form 2-(2-acetylthioalkoxy)-1-nitroalkane, which is then cyclized by treating with sodium hydroxide.

D. 4-oximino-1,3-dithiolane and 2-oximino-1,4-dithiane compounds can be prepared by reacting equivalent amounts of 2-haloalkanehydroxamoyl halide with the sodium salt of an appropriately substituted alkanedithiol in an aprotic solvent like benzene, methylene chloride or ethanol. For example, 2-oximino-3,3-dimethyl-1,4-dithiane can be prepared by adding 1,2-ethanedithiol to sodium ethoxide, thereby producing the sodium salt of 1,2-ethanedithiol in situ and then achieving cyclization by the addition of 2-chloro-2-methylpropionhydroxamoyl chloride.

The bis-(N-alkyl-N-fluorocarbonylamino)disulfide precursors can be conveniently prepared by reacting sulfur monochloride with N-alkylcarbamoyl fluoride in an aprotic solvent, such as toluene in the presence of an acid acceptor as for example triethylamine or pyridine. This procedure is described in more detail in U.S. Pat. No. 3,639,471.

Hydroxylated aryl compounds employed as reactants in the reaction of METHOD I are well known compounds that can be prepared by well known synthetic procedures or obtained from commercial sources.

The following specific examples are presented to particularly illustrate the invention:

EXAMPLE I

Preparation of 1-Methylthioacetaldehyde O-[N-methyl-N-(N'-methyl-N'-fluoroformylaminothiosulfenyl)carbamoyl]oxime.

To a solution of 10 g (0.046 m) of bis-(N-methyl-N-fluorocarbonylamino)disulfide in 50 ml of toluene was added dropwise with stirring a solution of 5.36 g (0.05 m) of 1-methylthioacetaldoxime and 4.68 g (0.046 m) of triethylamine dissolved in 150 ml of toluene. After stirring overnight at room temperature the reaction mixture was washed with water, dried over anhydrous magnesium sulfate and concentrated to afford 13.0 g of an yellow oil. Chromatographic purification afforded 7.23 g of 1-methylthioacetaldehyde O-[N-methyl-N-(N'-methyl-N-fluoroformylaminothiosulfenyl)carbamoyl]oxime which crystallized on standing. m.p. 41°–44° C.

Calc'd for $C_7H_{12}FN_3O_3S_3$: C, 27.89; H, 4.01; N, 13.94. Found: C, 27.90; H, 4.13; N, 13.90.

EXAMPLE II

Preparation of 1-(2-Cyanoethylthio)acetaldehyde O-[N-methyl-N-(N'-methyl-N-fluoroformylaminothiosulfenyl)carbamoyl]oxime.

To a solution of 15.0 g (0.104 m) of 1-(2-cyanoethylthio)cetaldoxime and 22.5 g (0.104 m) of bis(N-methyl-N-fluorocarbonylamino)disulfide in 200 ml of toluene, was added dropwise with stirring 10.52 g (0.104 m) of triethylamine dissolved in 300 ml of toluene. After stirring for 18 hrs. at ambient temperature, the reaction mixture was washed with water, dried over magnesium sulfate and concentrated under reduced pressure to afford 33.13 g of 1-(2-cyanoethylthio)acetaldehyde O-[N-methyl-N-(N'-methyl-N-fluoroformylaminothiosulfenyl) carbamoyl]oxime as an yellow oil.

Calc'd for $C_9H_{13}FN_4O_3S_3$: C, 31.75; H, 3.85; N, 16.46. Found: C, 32.93; H, 3.77; N, 16.35.

EXAMPLE III

Preparation of 2-Methyl-2-methylthioproppionaldehyde O-[N-methyl-N-(N'-methyl-N'-fluoroformylaminothiosulfenyl) carbamoyl]oxime.

To a solution of 8.11 g (0.0375 m) of bis(N-methyl-N-fluorocarbonylamino) disulfide and 3.79 g (0.0375 m) of triethylamine in 150 ml of toluene was added dropwise with stirring at 0°–10° C., a solution of 5.0 g (0.0375 m) of 2-methyl-2-methylthiopropionaldoxime dissolved in 100 ml of toluene. After stirring at ambient temperature for approximately 20 hrs., the reaction mixture was worked to afford an yellow oil which crystallized on standing. Recrystallization from isopropyl ether gave 3.87 g of 2-methyl-2-methylthiopropionaldehyde O-[N-methyl-N-(N'-methyl-N'-fluoroformylaminothiosulfenyl)carbamoyl] oxime as a white solid. m.p. 57.5°–60° C.

Calc'd. for $C_9H_{16}FN_3O_3S_3$: C, 32.81; H, 4.90; N, 12.75. Found: C, 32.85; H, 4.71; N, 12.70.

EXAMPLE IV

Preparation of 7-[N-Methyl-N-(N'-methyl-N'-fluoroformylaminothiosulfenyl)carbamoyloxy]-2,3-dihydro 2,2-dimethylbenzofuran.

Prepared according to the procedure described in Example III, by reacting 12.0 g (0.0731 m) of 2,3-dihydro2,2-dimethyl-7-benzofuranol with 15.81 g of bis-(N-methyl-N-fluorocarbonylamino)disulfide and 7.40 g (0.0731 m) of triethylamine in 300 ml of toluene. The conventional work-up afforded 27.55 g of 7-[N-methyl-N-(N'-methyl-N'-fluoroformylaminothiosulfenyl)carbamoyloxy]-2,3-dihydro2,2-dimethylbenzofuran as a reddish brown oil.

Calc'd. for $C_{14}H_{17}FN_2O_4S_2$: C, 46.65; H, 4.76; N, 7.77. Found: C, 46.85; H, 4.44; N, 7.84.

EXAMPLE V

Preparation of 4-tert-butylphenyl-N-methyl-N-(N'-methyl-N'-fluoroformylaminothiosulfenyl)carbamate Utilizing the procedure of EXAMPLE III, 20.0 g (0.133 m) of p-tert-butylphenol was reacted with 28.77 g (0.133 m) of bis-(N-methyl-N-fluorocarbonylamino)disulfide and 13.46 g (0.133 m) of triethylamine in 300 ml of toluene. After stirring at ambient temperature for approximately 20 hrs. The reaction mixture was washed dilute sodium hydroxide solution and water. The usual work-up afforded 42.6 g of 4-tert-butylphenyl-N-methyl-N-(N'-methyl-N'-fluorformylaminothiosulfenyl)carbamate as an oil.

Calc'd. for $C_{14}H_{19}FN_2O_3S_2$: C, 48.53; H, 5.53; N, 8.09. Found: C, 49.26; H, 5.31; N, 8.10.

The compounds of EXAMPLES VI–XI were prepared by the method of EXAMPLES I–V. The physical properties of the compounds of EXAMPLES VI–XI are set forth in TABLE I below:

TABLE I
ELEMENTAL ANALYSIS

| EXAMPLE | Compound | Molecular Formula | Calculated | | | Found | | |
|---|---|---|---|---|---|---|---|---|
| | | | C | H | N | C | H | N |
| VI | (H₃C)₂HC—O—C₆H₄—O—C(O)—N(CH₃)—S—C(CH₃)=N—OC(O)F | $C_{13}H_{17}FN_2O_4S_2$ | 44.81 | 4.92 | 8.04 | 45.58 | 4.99 | 7.99 |

TABLE I-continued
ELEMENTAL ANALYSIS

| EXAMPLE | Compound | Molecular Formula | Calculated | | | Found | | |
|---------|----------|-------------------|------|------|------|------|------|------|
| | | | C | H | N | C | H | N |
| VII | [structure: O-C(=O)-N(CH3)-S-S-N(CH3)-C(=O)-F with phenyl-CH(CH3)2 substituent] | $C_{13}H_{17}FN_2O_3S_2$ | 46.97 | 5.16 | 8.43 | 48.79 | 5.16 | 8.56 |
| VIII | [structure with O-CH2-C≡CH substituent on phenyl] | $C_{13}H_{13}FN_2O_4S_2$ | 45.34 | 3.80 | 8.14 | 45.73 | 3.71 | 8.46 |
| IX | [structure with naphthyl group] | $C_{14}H_{13}FN_2O_3S_2$ | 49.40 | 3.85 | 8.23 | 51.11 | 3.82 | 7.97 |
| X | $C_8H_{17}OC(=O)N(CH_3)-S-S-N(CH_3)-C(=O)F$ | $C_{12}H_{23}FN_2O_3S_2$ | 44.15 | 7.10 | 8.58 | 45.61 | 7.30 | 8.35 |
| XI | [structure with dithiane-NOC- group] | $C_8H_{12}FN_3O_3S_4$ | 27.81 | 3.50 | 12.16 | 28.88 | 3.71 | 11.96 |

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphis per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

SOUTHERN ARMYWORM LEAF SPRAY TEST

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, as sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

FLY BAIT TEST

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

MITE FOLIAGE SPRAY TEST

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two- and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living. growing potted cucumber for approximately three weeks. These cucumber plants were then removed from the pots, the soil washed from the roots and the amount of galling visually rated.

The results of these tests are set forth in Table I below. In these tests the pesticidal activity of the compounds against aphid, mite, Southern Armyworm, Bean Beetle and house fly was rated as follows:

A=excellent control
B=partial control
C=no control

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table II below.

toxicant will usually comprise a carrier and/or diluent, either liquid or solid.

TABLE II $$R_3O-\overset{O}{\underset{\|}{C}}-\overset{CH_3}{\underset{|}{N}}-S-S-\overset{CH_3}{\underset{|}{N}}-\overset{O}{\underset{\|}{C}}-F$$

BIOLOGICAL ACTIVITY

| R₃ | Insecticidal and Miticidal | | | | | Phytotoxicity | | | | |
|---|---|---|---|---|---|---|---|---|---|---|
|  | Aphid | Mite | Southern Armyworm | Mexican Bean Beetle | House-fly | Bean | Corn | Tomato | Cotton | Soybean |
| H₃C—C(SCH₃)=N— | A | A | A | A | A | 2 | 1 | 2 | 3 | 2 |
| H₃C—C(SCH₂CH₂CN)=N— | A | A | A | A | A | 2 | 1 | 1 | 1 | 2 |
| H₃CS—C(CH₃)(CH₃H)—C=N— | A | A | A | A | A | — | — | — | — | — |
| 2-(H₃C)₂C—O—(benzofuran) | A | A | A | A | A | 2 | 1 | 1 | 1 | 2 |
| 4-C(CH₃)₃-phenyl | C | C | C | A | C | 2 | 1 | 1 | 1 | 1 |
| 2-O—CH(CH₃)₂-phenyl | A | B | A | A | A | 3 | 1 | 1 | 2 | 3 |
| 3-CH(CH₃)₂-phenyl | A | C | A | A | A | 2 | 2 | 1 | 1 | 2 |
| 2-O—CH₂C≡CH-phenyl | A | A | A | A | A | 2 | 2 | 1 | 2 | 2 |
| naphthyl | A | C | A | A | B | 2 | 1 | 2 | 2 | 2 |
| dithiane-N= | A | C | A | A | A | — | — | — | — | — |

The results set forth in TABLE II clearly show the broad spectrum pesticidal activity of the compounds of this invention, as well as their reduced phytotoxicity. It will be understood that the insect and mite species employed in the above tests are merely representative of a wide variety of pests that can be controlled through the use of the compounds of this invention.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

$$R_3OC(=O)-N(R_1)-S-S-N(R_2)-C(=O)-F$$

wherein:
$R_1$ and $R_2$ are the same or different and are alkyl groups having from one to four carbon atoms;
$R_3$ is:
(A) alkyl, cycloalkyl, alkenyl or alkyenyl; or
(B) dihydrobenzofuranyl, naphthyl, tetrahydronaphthyl, benzothienyl, indanyl, benzodioxalanyl, benzofuranyl, benzodioxanyl, or methylenedioxyphenyl all of which may be either unsubstituted or substituted with one or more alkyl groups; or
(C) phenyl, either unsubstituted or substituted with one or more halo, cyano, nitro, cycloalkyl, alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino or alkoxy, or $$\underset{R_5}{\overset{R_4}{>}}C=N- \qquad (D)$$

or $AC=N$, wherein:
$R_4$ is hydrogen, alkyl, alkylthio, alkylsulfinyl, alkylsulfonyl or cyano;
$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl or dialkyoaminocarbonyl all of which may be unsubstituted or, except aminocarbonyl, substituted with one or more cyano, nitro, alkylthio, alkylsulfonyl, alkoxy, aminocarbonyl alkylaminocarbonyl, dialkylaminocarbonyl or $R_5$ is a $$R_6C(=O)-N(H)- \text{ or } R_6-C(=O)-N(alkyl)-$$

where $R_6$ is hydrogen, alkyl or alkoxy;
A is a divalent alkylene chain completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 3-oximino-thiophane, 2-oximinothiophane, 2-oximino-tetrahydro-1,4-oxazin-3-one, 2-oximino-1,3,5-trithiane, 4-oximino-1,3,5-oxadithiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring, wherein sulfur may be any of its oxidation states;

with the proviso that $R_3$, $R_4$, $R_5$ and $R_6$ substituents individually may not include more than eight aliphatic carbon atoms.

2. A compound according to claim 1 wherein $R_1$ and $R_2$ are methyl.

3. A compound according to claim 1 wherein $R_3$ is alkyl, naphthyl, dihydrobenzofuranyl, dihydrofuranyl substituted with one or more alkyl, 5, 6, 7, 8-tetrahydronaphthyl, phenyl or phenyl substituted with with one or more alkyl, alkynyloxy or alkoxy groups.

4. A compound according to claim 1 wherein $R_3$ is $$\underset{R_5}{\overset{R_4}{>}}C=N-.$$

5. A compound according to claim 4 wherein:
$R_4$ is hydrogen, alkylthio or cyano;
$R_5$ is alkyl, alkylthio, alkylsulfinyl, alkylsulfonyl, alkylthioalkyl, alkylsulfinylalkyl, alkylsulfonylalkyl or cyanoalkylthio.

6. A compound according to claim 1 wherein $R_3$ is $AC=N-$.

7. A compound according to claim 6 wherein A is a divalent alkylene claim having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxazin-3-one, 2-oximino-1,3,5-trithiane, 4-oximino-1,3,5-oxathiane, 2-oximino-1,4-oxathiane, 4-oximino-1,3-oxathiolane, 2-oximino-thiazolidin-3-one, 2-oximino-1,3-thiazolidin-4-one or 2-oximino-tetrahydro-1, 4-thiazin-5-one ring structure, wherein sulfur may be in any of its oxidation states.

8. 1-Methylthioacetaldehyde 0-[N-methyl-N-(N'-methyl-N'-fluoroformylaminothiosulfenyl)carbamoyl)-]oxime.

9. 2-Methyl-2-methylthiopropionaldehyde 0-[N-methyl-N-(N'-methyl-N'-fluoroformylaminothiosulfenyl)carbamoyl]oxime.

10. 7-[N-Methyl-N-(N'-methyl-N'-fluoroformylaminothiosulfenyl)carbamoyloxy]-2,3-dihydro-2,2-dimethylbenzofuran.

11. An insecticidal and miticidal composition comprising an acceptable carrier and as the active toxicant an insecticidally and miticidally effective amount of a compound of the formula:

$$R_3OC(=O)-N(R_2)-S-S-N(R_1)-C(=O)-F$$

wherein:
$R_1$ and $R_2$ are the same or different and are alkyl groups having from one to four carbon atoms; $R_3$ is:
 (A) alkyl, cycloalkyl, alkenyl or alkylenyl; or
 (B) dihydrobenzofuranyl, naphthyl, tetrahydronaphthyl, benzothienyl, indanyl, benzodioxalanyl, benzofuranyl, benzodioxanyl, or methylenedioxyphenyl, all of which may be either unsubstituted or substituted with one or more alkyl groups; or
 (C) phenyl, either unsubstituted or substituted with one or more halo, cyano, nitro, cycloalkyl, alkyl, alkylthio, alkynyl, alkenyl, alkylsulfinyl, alkylsulfonyl, alkylsulfonylalkyl, amino, alkylamino, dialkylamino, alkynlthio, alkenylthio, alkoxycarbonylamino, trihalomethyl, dialkylaminoalkyleneamino, formamidino, alkoxy, $$R_4\!\!\!\underset{R_5}{\diagdown}\!\!C{=}N- \quad (D)$$

or A $\frown$ C=N, wherein:
$R_4$ is hydrogen, alkyl, alkylthio, alkylsulfinyl, alkylsulfonyl or cyano;
$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl or dialkylaminocarbonyl all of which may be unstituted or, except aminocarbonyl, substituted with one or more cyano, nitro, alkylthio, alkylsulfonyl, alkoxy, aminocarbonyl, alkylaminocarbonyl, dialkylaminocarbonyl, or $R_5$ is a $$R_6C(=O)-N(H)- \text{ or } R_6-C(=O)-N(\text{alkyl})-$$

group where $R_6$ is hydrogen, alkyl or alkoxy;
A is a divalent alkylene chain completing a 2-oximino-1,4-dithiane, 2-oximino-1,3-dithiane, 4-oximino-1,3dithiolane, 2-oximino-1,4-dioxane,2-oximino-tetrahydro-1,4-thiazine-3-one, 2-oximino-1,3-dithiolane, 3-oximino-thiophane, 2-oximinothiophane, 2-oximino-tetrahydro-1,4-oxazin-3-one, 2-oximino-1,3,5-trithiane, 4-oximino-1,3,5-oxadithiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring, wherein sulfur may be in any of its oxidation states;
with the proviso that $R_3$, $R_4$, $R_5$ and $R_6$ substituents individually may not include more than eight aliphatic carbon atoms.

12. A method of controlling insects and mites which comprises subjecting them to an insecticidally or miticidally effective amount of a compound of the formula:

$$R_3OC(=O)-N(R_2)-S-S-N(R_1)-C(=O)-F$$

wherein:
$R_1$ and $R_2$ are the same or different and are alkyl groups having from one to four carbon atoms; $R_3$ is:
 (A) alkyl, cycloalkyl, alkenyl or alkyenyl; or
 (B) dihydrobenzofuranyl, naphthyl, tetrahydronaphthyl, benzothienyl, indanyl, benzodioxalanyl, benzofuranyl, benzodioxanyl, or methylenedioxphenyl all of which may be either unsubstituted or substituted with one or more alkyl groups; or
 (C) phenyl, either unsubstituted or substituted with one or more halo, cyano, nitro, cycloalkyl, alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino, alkoxy, $$R_4\!\!\!\underset{R_5}{\diagdown}\!\!C{=}N- \quad (D)$$

or A $\frown$ C=N, wherein:
$R_4$ is hydrogen, alkyl, alkylthio, alkylsulfinyl, alkylsulfonyl or cyano;
$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl or dialkylaminocarbonyl all of which may be unsubstituted or, except aminocarbonyl, substituted with one or more cyano, nitro, alkylthio, alkylsulfonyl, alkoxy, aminocarbonyl alkyl aminocarbonyl, dialkylaminocarbonyl or $R_5$ is a

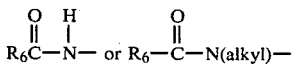

where $R_6$ is hydrogen, alkyl or alkoxy;

A is a divalent alkylene chain completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 3-oximino-thiophane, 2-oximinothiophane, 2-oximino-tetrahydro-1,4-oxazin-3-one, 2-oximino-1,3,5-trithiane, 4-oximino-1,3,5-oxadithiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring, wherein sulfur may be in any of its oxidation states;

with the proviso that $R_3$, $R_4$, $R_5$ and $R_6$ substituents individually may not include more than eight aliphatic carbon atoms.

13. A method of preparing a compound of the formula:

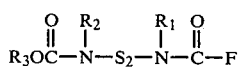

which comprises reacting a compound of the formula:

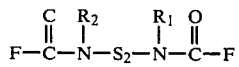

with a compound of the formula:

$R_3OH$ in the presence of an acid acceptor, wherein $R_1$ and $R_2$ are the same or different and are alkyl groups having from one to four carbon atoms;

$R_3$ is:
(A) alkyl, cycloalkyl, alkenyl or alkyenyl; or
(B) dihydrobenzofuranyl, naphthyl, tetrahydronaphthyl, benzothienyl, indanyl, benzodioxalanyl, benzofuranyl, benzodioxanyl, or methylenedioxyphenyl all of which may be either unsubstituted or substituted with one or more alkyl groups; or
(C) phenyl, either unsubstituted or substituted with one or more halo, cyano, nitro, cycloalkyl, alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino, alkoxyl; or

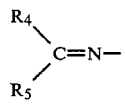 (D)

or C=N, wherein:

$R_4$ is hydrogen, alkyl, alkylthio, alkylsulfinyl, alkylsulfonyl or cyano;

$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl or dialkylaminocarbonyl all of which may be unsubstituted or, except aminocarbonyl, substituted with one or more cyano, nitro, alkylthio, alkylsulfonyl, alkoxy, aminocarbonyl, alkylaminocarbonyl, dialkylaminocarbonyl or $R_5$ is a

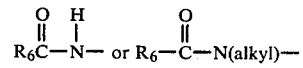

group where $R_6$ is hydrogen, alkyl or alkoxy;

A is a divalent alkylene chain completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 3-oximino-thiophane, 2-oximinothiophane, 2-oximino-tetrahydro-1,4-oxazin-3-one, 2-oximino-1,3,5-trithiane, 4-oximino-1,3,5-oxadithiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring, wherein sulfur may be in any of its oxidation states; with the proviso that $R_3$, $R_4$, $R_5$ and $R_6$ substituents individually may not include more than eight aliphatic carbon atoms.

14. A compound of the formula:

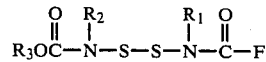

wherein:

$R_1$ and $R_2$ are the same or different and are alkyl groups having from one to four carbon atoms;

$R_3$ is

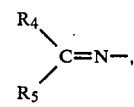

wherein:

$R_4$ is hydrogen, alkyl, alkylthio, alkylthio, alkylsulfinyl, alkylsulfonyl, alkylsulfonyl or cyano;

$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl, or dialkylaminocarbonyl, all of which may be unsubstituted or, except aminocarbonyl, substituted with one or more cyano, nitro, cycloalkyl, alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino, or alkoxy;

with the proviso that $R_3$, $R_4$, $R_5$, and $R_6$ substituents individually may not include more than eight aliphatic carbon atoms.

15. A compound according to claim 14 wherein $R_1$ and $R_2$ are methyl.

16. A compound according to claim 14, wherein $R_4$ is hydrogen, alkylthio or cyano.

17. A compound according to claim 14 wherein $R_5$ is alkyl, alkylthio, alkylsulfinyl, alkylsulfonyl, alkylthioalkyl, alkylsulfinylalkyl, alkylsulfonylalkyl, or cyanoalkylthio.

18. A compound according to claim 14 wherein:
$R_1$ and $R_2$ are methyl;
$R_4$ is hydrogen, alkylthio or cyano;
$R_5$ is alkyl, alkylthio, alkylsulfinyl, alkylsulfonyl alkylthioalkyl, alkylsulfinylalkyl, alkylsulfonylalkyl, or cyanoalkylthio.

19. An insecticidal and miticidal composition comprising an acceptable carrier and as the active toxicant an insecticidally and miticidally effective amount of a compound according to claim 14.

20. An insecticidal and miticidal composition comprising an acceptable carrier and as the active toxicant an insecticidally and miticidally effective amount of a compound according to claim 15.

21. An insecticidal and miticidal composition comprising an acceptable carrier and as the active toxicant an insecticidally and miticidally effective amount of a compound according to claim 15.

22. An insecticidal and miticidal composition comprising an acceptable carrier and as the active toxicant an insecticidally and miticidally effective amount of a compound according to claim 16.

23. An insecticidal and miticidal composition comprising an acceptable carrier and as the active toxicant an insecticidally and miticidally effective amount of a compound according to claim 17.

24. A method of controlling insects and mites which comprises subjecting them to an insecticidally or miticidally effective amount of a compound according to claim 14.

25. A method of controlling insects and mites which comprises subjecting them to an insecticidally or miticidally effective amount of a compound according to claim 15.

26. A method of controlling insects and mites which comprises subjecting them to an insecticidally or miticidally effective amount of a compound according to claim 16.

27. A method of controlling insects and mites which comprises subjecting them to an insecticidally or miticidally effective amount of a compound according to claim 17.

28. A method of controlling insects and mites which comprises subjecting them to an insecticidally or miticidally effective amount of a compound according to claim 18.

29. A method of preparing a compound of the formula

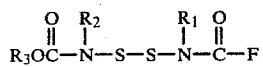

which comprises reacting a compound of the formula:

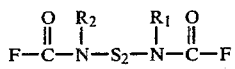

with a compound of the formula:

$R_3OH$ in the presence of an acid acceptor wherein:
$R_1$ and $R_2$ are the same or different and are alkyl groups having from one to four carbon atoms;
R is

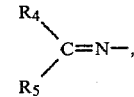

wherein:
$R_4$ is hydrogen, alkyl, alkylthio, alkylthio, alkylsulfinyl, alkylsulfonyl or cyano;
$R_5$ is alkyl, alkylthio, alkylsulfinyl, alkylsulfonyl, alkoxy, alkanoyl, aroyl, alkoxycarbonyl, phenyl, aminocarbonyl, alkylaminocarbonyl, or dialkylaminocarbonyl, all of which may be unsubstituted or, except aminocarbonyl, substituted with one or more cyano, cycloalkyl alkyl, alkylthio, alkynyl, alkenyl, alkylsulfinyl, alkylsulfonyl, alkylthioalkyl, alkylsulfinylalkyl, alkylsulfonylalkyl, amino, alkylamino, dialkylamino, alkynylthio, alkenylthio, alkoxycarbonylamino, trihalomethyl, dialkylaminoalkyleneamino, formamidino, or alkoxy; with the proviso that $R_3$, $R_4$, $R_5$, and $R_6$ substituents individually may not include more than either aliphatic carbon atoms.

30. A compound of the formula:

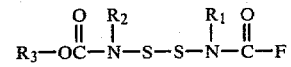

wherein:
$R_1$ and $R_2$ are the same or different and are alkyl groups having from one to four carbon atoms;
$R_3$ is

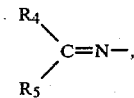

wherein
$R_4$ is hydrogen, alkyl, alkylthio, alkylsulfinyl or alkylsulfonyl;
$R_5$ is alkyl, alkylthio, alkylsulfinyl, alkoxy, alkanoyl, aroyl phenyl, aminocarbonyl, alkylaminocarbonyl, or dialkylaminocarbonyl, all of which may be unsubstituted or, except aminocarbonyl, substituted with one or more nitro cycloalkyl, alkyl, alkylthio, alkynyl, alkenyl, alkylsulfinyl, alkylsulfonyl, alkylthioalkyl, alkylsulfinylalkyl, amino, alkylamino, dialkylamino, alkynylthio, alkenylthio, trihalomethyl, dialkylaminoalkyleneamino, formamidino or alkoxy; with the proviso that $R_3$, $R_4$, $R_5$ and $R_6$ substituents individually may not include more than eight aliphatic carbon atoms.

31. An insecticidal and miticidal composition comprising an acceptable carrier and as the active toxicant an unsecticidally or miticidally effective amount of a compound according to claim 30.

32. A method of controlling insects and mites which comprises subjecting them to an insecticidally or miticidally effective amount of a compound according to claim 30.

* * * * *